US00PP28366P3

(12) United States Plant Patent
White

(10) Patent No.: US PP28,366 P3
(45) Date of Patent: Sep. 12, 2017

(54) APPLE TREE NAMED 'PREMA34'

(50) Latin Name: ***Malus domestica* Mill**
Varietal Denomination: PremA34

(71) Applicant: Prevar Limited, Hastings (NZ)

(72) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 14/999,304

(22) Filed: Apr. 21, 2016

(65) Prior Publication Data

US 2016/0316596 P1 Oct. 27, 2016

Related U.S. Application Data

(60) Provisional application No. 62/178,992, filed on Apr. 24, 2015.

(51) Int. Cl.
*A01H 5/08* (2006.01)

(52) U.S. Cl.
USPC ..... Plt./161

(58) Field of Classification Search
USPC ..... Plt./161
See application file for complete search history.

(56) References Cited

PUBLICATIONS

PLUTO Plant Variety Database Mar. 17, 2017. p. 1.*

* cited by examiner

*Primary Examiner* — Annette Para
(74) *Attorney, Agent, or Firm* — Michelle Bos Legal LLC

(57) ABSTRACT

A new and distinct apple tree named 'PremA34' is disclosed. The new apple is notable for its attractive appearance, superb texture, improved flavor and scab resistance.

2 Drawing Sheets

Latin name of the genus and species of the plant claimed: *Mallus domestica* Mill.

Variety denomination: 'PremA34'.

BRIEF DESCRIPTION OF THE PHOTOGRAPHS

Figure 1:
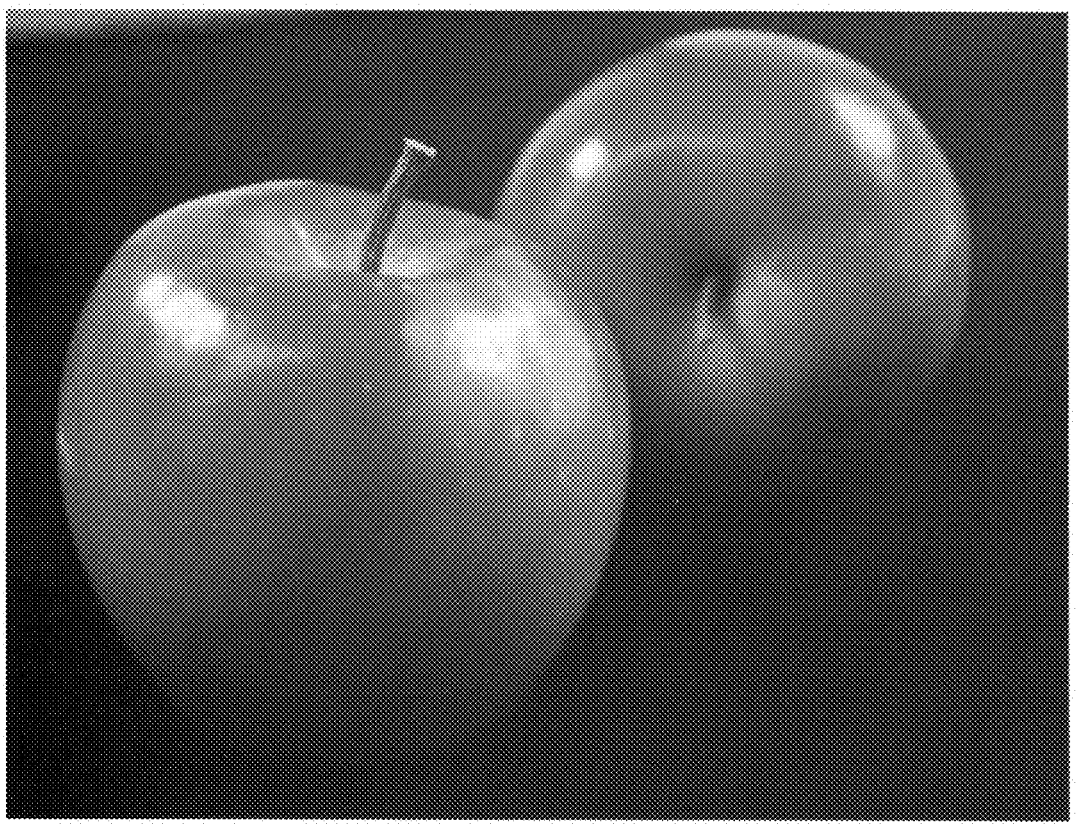
Figure 2:
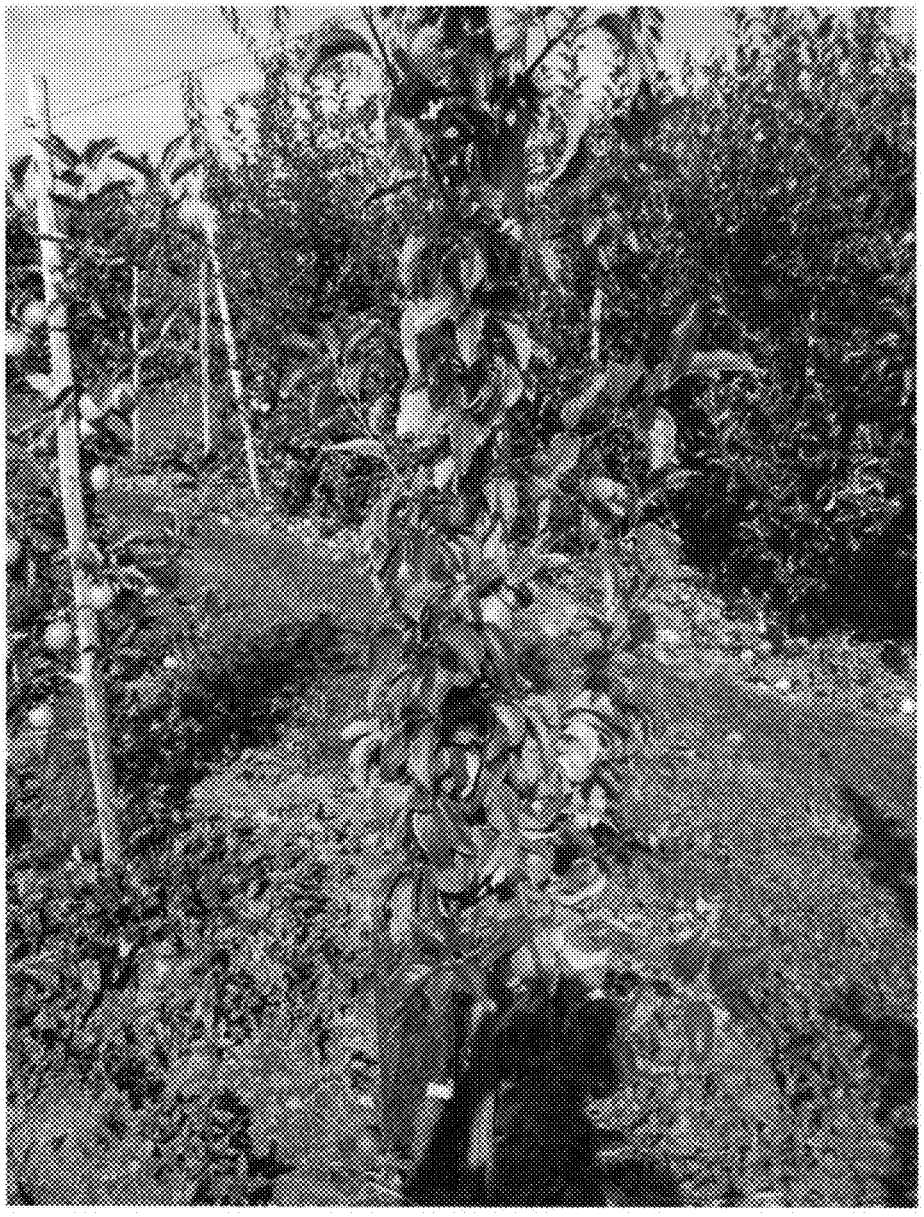

FIG. 1 shows the fruit of a 'PremA34' apple tree;
FIG. 2 shows a PremA34' apple tree;

BRIEF DESCRIPTION OF THE VARIETY

The new variety of apple tree 'PremA34' was created in the course of a planned breeding program carried out at The New Zealand Institute for Plant and Food Research, Hawkes Bay, New Zealand. 'PremA34' originated as a result of a controlled cross of 'Sciros' (seed parent, unpatented) and 'A038R02T119', also known as 'Pinkie' (pollen parent, unpatented). 'PremA34' was selected as a single plant from among a population of seedlings derived from the parents. Asexual propagation by budding was first carried out in New Zealand. The variety has since been observed over a number of asexually propagated generations, and has been found to remain true to type.

'PremA34' is distinguished from similar variety 'Scifresh' as shown in Table 1 below.

TABLE 1

Comparison of 'PremA34' to 'Scifresh'

| Characteristic | Scifresh | PremA34 |
|---|---|---|
| Flavor | Sweet-acid | Sweet-mild |
| Appearance | Red stripe | Pink/red blush |
| Scab resistance | Nil | Has resistance |

DETAILED BOTANICAL DESCRIPTION OF THE VARIETY

The following detailed botanical description is based on observations made during the 2015 growing season at Parker, Wash. on five year old trees. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Ramified; Habit semi-spreading; Vigor moderate; Height 2.4 M; Diameter 1 m; Trunk diameter at 30 cm above the graft union 6 cm; Bark texture smooth with rough lenticels; Bark coloration greyed orange 173B with black 202D overcolor; Lenticels 0.3 cm long; Lenticel color black 202C.

Branch: Length 90 cm; Diameter 2 cm; Crotch angle 50°; Color greyed orange 173B; Lenticel diameter 0.2 cm; Lenticel color black 202C; 18 lenticels per square inch 18.

One year old shoot: Length 43 cm; Color greyed orange 173A; Diameter 6 mm; Internode length 6 cm; Lenticels 1 mm; Lenticel color yellow 1 D; 9 lenticels per square inch 9.

Flowers:

*Bud.*—Quantity per spur 4; length 1.2 cm; diameter 7 mm; color red-purple 63B.

*Petals.*—Quantity per flower 5; length 2.8 cm; diameter 2 cm; margin smooth, overlapping; color of upper surface red-purple 63D and white 155C.

*Flower*.—Color at balloon stage red-purple 63C; Diameter 5 cm.

*Pistils*.—Size 1.2 cm; Color yellow 2D.

*Sepals*.—Quantity per flower 5; length 1 cm; width 4 mm; color yellow-green N144B.

*Pedicel*.—Length 4 cm; diameter 1 mm; color yellow-green N144B.

*Anthers*.—Quantity per flower 13; length 1 mm; pollen color yellow-green 154D.

*Stigma*.—Size 1 mm; Color yellow-green 154D.

*Style*.—Length 1.1; color yellow 2D.

*Ovary*.—Length 6 mm; width 4 mm; color green 138A.

*Leaves*.—Length 10 cm; Width 5 cm; Blade margin serrated; Apex pointed; Base shape pointed; Upper surface color yellow-green 144A; Under surface color yellow-green 146C; Attitude in relation to shoot 70°.

*Petiole*.—Length 3 cm; Diameter 2 mm; Color yellow-green 145C.

Fruit: Shape — Oblate; Length of sepal 5 mm; Depth of eye basin 3 cm; Length of stalk 3.5 cm; Width of stalk cavity 2.5 cm; Depth of stalk cavity 1.5 cm; Size of lenticels 1 mm; Relative area of over color — very large; Background color of skin yellow 1 D; Overcolor of skin red 46D with some red 48A; Pattern of over color — Only solid blush; Flesh texture crisp; Juiciness medium; Flesh color white 155B; Stem color yellow-green 145B; Seeds — Quantity per fruit 14; Seed color greyed-orange 166A.

*Time of beginning of flowering*.—April $4^{th}$.

*Time of full bloom*.—April $10^{th}$.

*Time of eating maturity*.—Medium.

*Other characteristics*.—VF scab resistance.

Use: Fresh Market.

I claim:

1. A new and distinct apple tree substantially as shown and described herein.

* * * * *